US012733880B2

(12) United States Patent
Banerjee et al.

(10) Patent No.: US 12,733,880 B2
(45) Date of Patent: Sep. 15, 2026

(54) METHOD AND A SYSTEM FOR DETERMINING QUALITY OF PHOTOPLETHYSMOGRAM (PPG) SIGNAL

(71) Applicant: Tata Consultancy Services Limited, Mumbai (IN)

(72) Inventors: Tanushree Banerjee, Kolkata (IN); Rahul Dasharath Gavas, Bangalore (IN); Mithun Basaralu Sheshachala, Bangalore (IN); Somnath Karmakar, Kolkata (IN); Ramesh Kumar Ramakrishnan, Bangalore (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 525 days.

(21) Appl. No.: 17/804,269

(22) Filed: May 26, 2022

(65) Prior Publication Data

US 2023/0000442 A1 Jan. 5, 2023

(30) Foreign Application Priority Data

May 27, 2021 (IN) ............................ 202121023570

(51) Int. Cl.
*A61B 5/00* (2006.01)
*A61B 5/0205* (2006.01)
(Continued)

(52) U.S. Cl.
CPC .......... *A61B 5/7221* (2013.01); *A61B 5/0205* (2013.01); *A61B 5/02416* (2013.01);
(Continued)

(58) Field of Classification Search
CPC . A61B 5/0205; A61B 5/02416; A61B 5/0816; A61B 5/7221; A61B 5/725;
(Continued)

(56) References Cited

U.S. PATENT DOCUMENTS 10,490,309 B1 * 11/2019 McNair .................. A61B 5/021
10,910,110 B1 * 2/2021 McNair ............. A61B 5/02035
(Continued)

OTHER PUBLICATIONS

K. Venu Madhav, et al., "A model based method for deriving respiratory activity from photoplethysmographic signals," 10th International Conference on Information Science, Signal Processing and their Applications (ISSPA 2010), Kuala Lumpur, Malaysia, 2010, pp. 312-315, doi: 10.1109/ISSPA.2010.5605464. (Year: 2010).*
(Continued)

*Primary Examiner* — Allen Porter
*Assistant Examiner* — Shreya Anjaria
(74) *Attorney, Agent, or Firm* — Finnegan, Henderson, Farabow, Garrett & Dunner, LLP

(57) ABSTRACT

This disclosure relates generally to a method and a system for determining quality of PPG signal. The PPG signals are extensively used for deducing health parameters of patients to infer the physiological conditions of heart, blood pressure, breathing patterns of the patients. However, analysis based on PPG signals is extremely challenging and is accurate only on high quality PPG signals. However, the existing techniques for determining quality of PPG signal (that are collected using wearable devices) require huge training or use complicated algorithms and cannot be used for real-time analysis. The disclosed methods and system for PPG quality assessment is based on the frequency domain analysis, wherein heart and respiratory components in the frequency spectrum are used effectively to derive the quality checker metric which is further used to estimate a plurality of optimal thresholds that is used for determining the quality of PPG signals at real-time.

7 Claims, 8 Drawing Sheets

(51) Int. Cl.
*A61B 5/024* (2006.01)
*A61B 5/08* (2006.01)
*G16H 40/67* (2018.01)
*G16H 50/70* (2018.01)

(52) U.S. Cl.
CPC ............ *A61B 5/725* (2013.01); *A61B 5/7278* (2013.01); *G16H 40/67* (2018.01); *G16H 50/70* (2018.01); *A61B 5/0816* (2013.01); *A61B 2505/03* (2013.01)

(58) Field of Classification Search
CPC . A61B 5/7267; A61B 5/7278; A61B 2505/03; G16H 40/67; G16H 50/20; G16H 50/70
See application file for complete search history.

(56) References Cited

U.S. PATENT DOCUMENTS

| | | | | |
|---|---|---|---|---|
| 2011/0077531 | A1* | 3/2011 | Watson ................ | A61B 5/0205 702/19 |
| 2014/0243628 | A1* | 8/2014 | Ochs .................... | A61B 5/0205 600/324 |
| 2018/0338727 | A1* | 11/2018 | Mukhopadhyay ..... | A61B 5/721 |
| 2019/0133533 | A1* | 5/2019 | Alam ................... | A61B 5/6898 |
| 2020/0323493 | A1* | 10/2020 | Arora ..................... | A61B 5/725 |

OTHER PUBLICATIONS

Li Q, Clifford GD. Signal quality and data fusion for false alarm reduction in the intensive care unit. J Electrocardiol. Nov.-Dec. 2012; 45(6):596-603. doi: 10.1016/j.jelectrocard.2012.07.015. Epub Sep. 7, 2012. PMID: 22960167. (Year: 2012).*

Orphanidou, Christina et al., "Signal-Quality Indices for the Electrocardiogram and Photoplethysmogram: Derivation and Applications to Wireless Monitoring", IEEE Journal of Biomedical and Health Informatics, Date: 2014, vol. 19(3), Publisher: IEEE, Link: https://www.researchgate.net/publication/264395822_Signal-Quality_Indices_for_the_Electrocardiogram_and_Photoplethysmogram_Derivation_and_Applications_to_Wireless_Monitoring/link/55a4f2a508ae81aec91324a3/download.

Zhang, Jie et al., Title: Photoplethysmogram Signal Quality Assessment Using Support Vector Machine and Multi-Feature Fusion, Title of the item: Journal of Medical Imaging and Health Informatics, Date: 2018, Publisher: Research Gate, https://www.researchgate.net/publication/330930684_Photoplethysmooram_Signal_Quality_Assessment_Using_Support_Vector_Machine_and_Multi-Feature_Fusion/link/5ce957c3458515712ec343da/download.

* cited by examiner

METHOD AND A SYSTEM FOR DETERMINING QUALITY OF PHOTOPLETHYSMOGRAM (PPG) SIGNAL

PRIORITY CLAIM

This U.S. patent application claims priority under 35 U.S.C. § 119 to: India Application No. 202121023570, filed on 27 May 2021. The entire contents of the aforementioned application are incorporated herein by reference.

TECHNICAL FIELD

The disclosure herein generally relates to the field of analysis of photoplethysmograph (PPG) signal, and, more particularly, to a method and a system for determining quality of PPG signal.

BACKGROUND

The healthcare systems have seen a huge technical revolution in the recent times due to the advancement in the areas of artificial intelligence and internet of things (IoT). Several fitness parameters of a subject such as heart arrhythmias, sleep tracking, hydration monitoring, SpO2 content (oxygen saturation in blood), heart rate, respiration rate, blood pressure, can be precisely estimated from photoplethysmograph (PPG) signals. The PPG signals are extensively used for deducing health parameters of patients to infer the physiological conditions of heart, blood pressure, and breathing patterns of the patients.

Analysis and estimations based on PPG signals is extremely challenging and is accurate only on high quality PPG signals. However, the PPG signal which can be derived easily from wearable devices such as pulse oximeters smart phones may not be of high-quality and has a high probability of getting corrupted with motion artifacts of a subject. Hence there is a requirement for a simple robust mechanism to assess/analyze the quality of the PPG signal collected using a wearable device.

State-of-art methods for determining quality of PPG signal are based on supervised machine learning, extraction of time/frequency domain features. However, the state-of-art methods can be implemented only on a particular time duration at offline scenarios and also requires a huge amount of training data. Further some state-of-art techniques to classify PPG signals also extract certain features at a pulse level, but these may not be very reliable in cases where the signal is highly contaminated with artifacts such that pulses cannot be segregated efficiently. Hence, considering the challenges with respect to existing state-of-art techniques, there is a need for real-time, simple and easily deployable solution for PPG signal classification technique.

SUMMARY

Embodiments of the present disclosure present technological improvements as solutions to one or more of the above-mentioned technical problems recognized by the inventors in conventional systems. For example, in one embodiment, a method for determining quality of PPG signal is provided.

The system is further configured for receiving a plurality of raw input signals from a device, via one or more hardware processors, wherein the plurality of raw input signals comprises a plurality of data sets associated with a PPG signal of a plurality of subjects. The system is further configured to filter the plurality of raw input signals to obtain a plurality of filtered signals, via the one or more hardware processors, wherein the plurality of raw input signals is filtered based on a filtering technique. The system is further configured to extract a plurality of heart frequency components and a plurality of breathing frequency components from the plurality of raw input signals and the plurality of filtered signals via the one or more hardware processors, based on an extraction technique. The system is further configured to determine a plurality of metrices using the plurality of heart frequency components and the plurality of breathing frequency components, via the one or more hardware processors, for a pre-defined time interval. The system is further configured to estimate a plurality of optimum thresholds using the plurality of metrices, via the one or more hardware processors, based on a differential evolutionary optimization technique. The system is further configured to determine the quality of the plurality of input signals at real time via the one or more hardware processors, wherein the quality of the plurality of input signals is determined as one of bad signal and a good signal based on a PPG signal classification technique using the plurality of optimum thresholds.

In another aspect, a method for determining quality of PPG signal is provided. The method includes receiving a plurality of raw input signals from a device, wherein the plurality of raw input signals comprises a plurality of data sets associated with a PPG signal of a plurality of subjects. The method further includes filtering the plurality of raw input signals to obtain a plurality of filtered signals, wherein the plurality of raw input signals is filtered based on a filtering technique. The method further includes extracting a plurality of heart frequency components and a plurality of breathing frequency components from the plurality of raw input signals and the plurality of filtered signals based on an extraction technique. The method further includes determining a plurality of metrices using the plurality of heart frequency components and the plurality of breathing frequency components for a pre-defined time interval. The method further includes estimating a plurality of optimum thresholds using the plurality of metrices based on a differential evolutionary optimization technique. The method further includes determining the quality of the plurality of input signals at real time, wherein the quality of the plurality of input signals is determined as one of bad signal and a good signal based on a PPG signal classification technique using the plurality of optimum thresholds.

In yet another aspect, a non-transitory computer readable medium for determining quality of PPG signal is provided. The program includes receiving a plurality of raw input signals from a device, wherein the plurality of raw input signals comprises a plurality of data sets associated with a PPG signal of a plurality of subjects. The program further includes filtering the plurality of raw input signals to obtain a plurality of filtered signals, wherein the plurality of raw input signals is filtered based on a filtering technique. The program further includes extracting a plurality of heart frequency components and a plurality of breathing frequency components from the plurality of raw input signals and the plurality of filtered signals based on an extraction technique. The program further includes determining a plurality of metrices using the plurality of heart frequency components and the plurality of breathing frequency components for a pre-defined time interval. The program further includes estimating a plurality of optimum thresholds using plurality of metrices based on a differential evolutionary optimization technique. The program further includes determining the quality of the plurality of input signals at real time, wherein the quality of the plurality of input signals is determined as one of bad signal and a good signal based on a PPG signal classification technique using the plurality of optimum thresholds.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
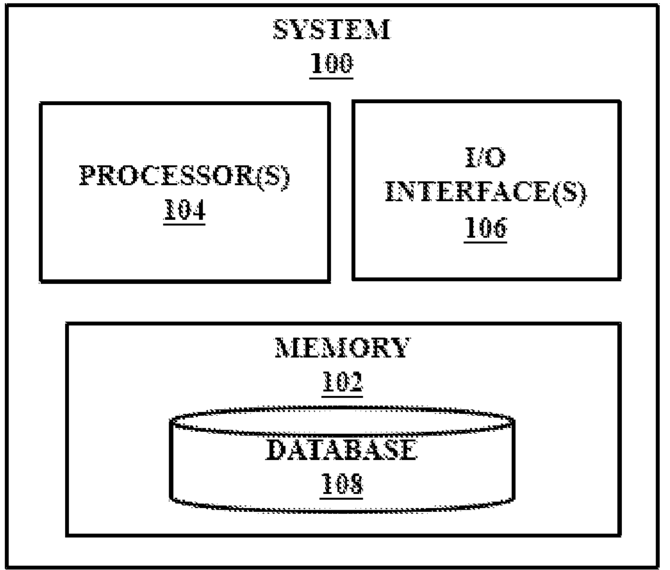
FIG. 1 illustrates an exemplary system for determining quality of PPG signal according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

FIG. 1 is an exemplary block diagram of a system 100 for determining quality of PPG signal in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of the system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 is configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, a touch user interface (TUI) and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Further, the memory 102 may include a database 108 configured to include information regarding for determining quality of PPG signal. The memory 102 may comprise information pertaining to input(s)/output(s) of each step performed by the processor(s) 104 of the system 100 and methods of the present disclosure. In an embodiment, the database 108 may be external (not shown) to the system 100 and coupled to the system via the I/O interface 106.

Figure 2:
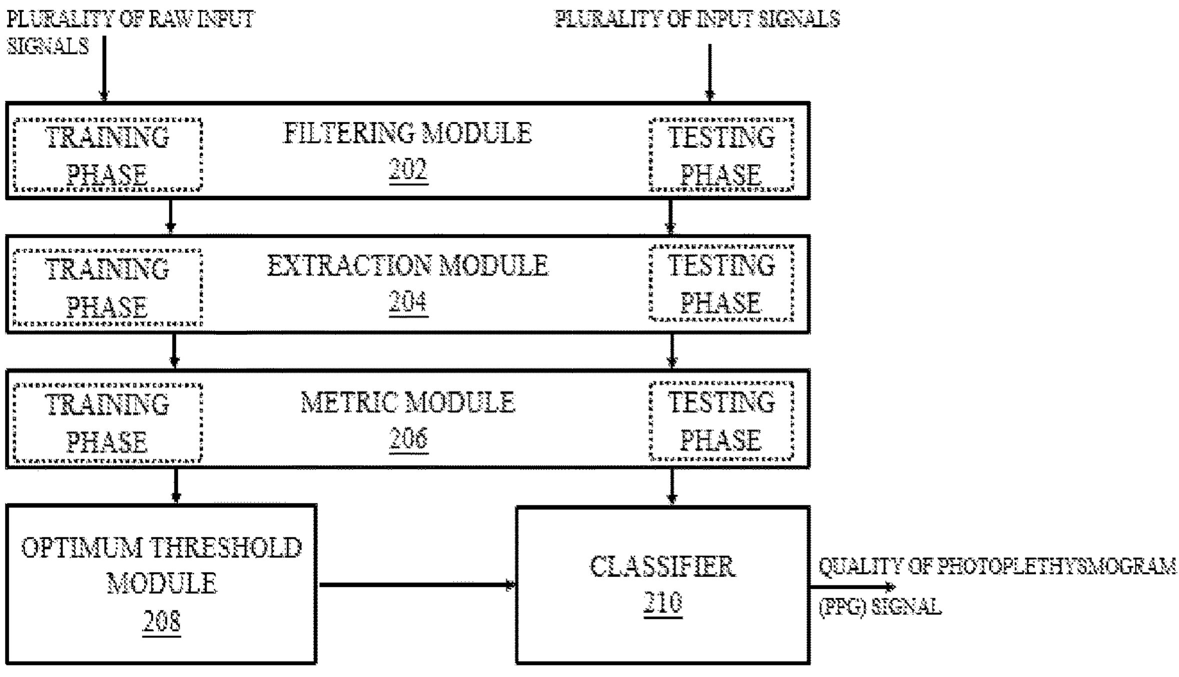
FIG. 2 is a functional block diagram for determining quality of PPG signal according to some embodiments of the present disclosure.
Figure 3A:
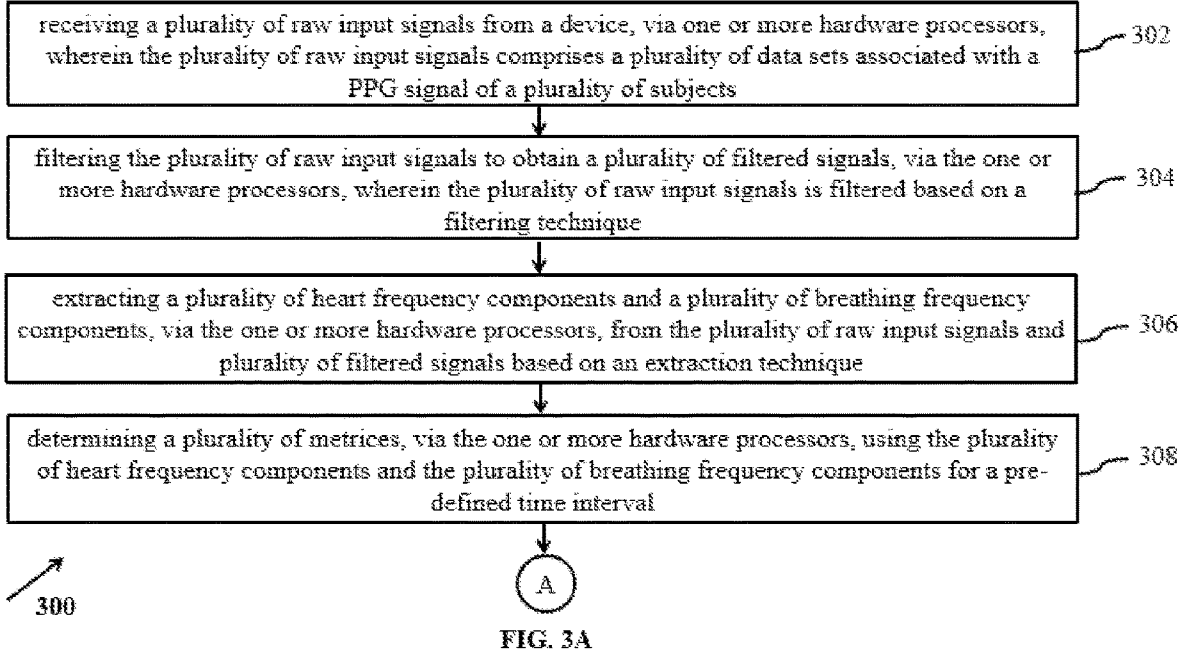
FIG. 3A and FIG. 3B is a flow diagram for determining quality of PPG signal, using the system of FIG. 1, in accordance with some embodiments of the present disclosure.
Figure 3B:
Figure 3B:
Figure 3B:

Functions of the components of system 100 are explained in conjunction with functional overview of the system 100 in FIG. 2 and flow diagram of FIG. 3A and FIG. 3B for determining quality of PPG signal.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

FIG. 2 is an example functional block diagram of the various modules of the system of FIG. 1, in accordance with some embodiments of the present disclosure. As depicted in the architecture, the FIG. 2 illustrates the functions of the modules of the system 100 that includes determining quality of PPG signal, wherein the PPG signals are collected from an edge computing scenario using one of: wearable, Intensive Care Unit (ICU), and medical grade devices.

The quality PPG signals are determined by processing the PPG signals in several steps including a filtering technique, an extraction technique, a differential evolutionary optimization technique to finally estimate a plurality of optimum thresholds. The plurality of optimum thresholds is used for determining quality of PPG signal.

As depicted in FIG. 2, the functional system 200 of system 100 system 200 is configured to function in a training phase and a testing phase based on a user requirement. During the training phase, a plurality of optimum thresholds are estimated based on a differential evolutionary optimization technique using heart frequency components and respiratory frequency components. Further, during the testing phase the plurality of optimum thresholds are used for determining quality of PPG signal, wherein the PPG signals are collected from an edge computing scenario using one of: wearable, Intensive Care Unit (ICU), and medical grade devices.

The system 200 further comprises a filtering module 202 configured for (a) receiving a plurality of raw input signals associated with a PPG signal of a plurality of subjects and (b) filtering the plurality of raw input signals to obtain a plurality of filtered signal based on a filtering technique. The system 200 further comprises an extraction module 204 configured for extracting a plurality of heart frequency components and a plurality of breathing frequency components from the plurality of raw input signals and the plurality of filtered signals based on an extraction technique. The system 200 further comprises a metric module 206 configured for determining a plurality of metrices, using the plurality of heart frequency components and the plurality of breathing frequency components for a pre-defined time interval. The system 200 further comprises an optimum threshold module 208 configured for estimating a plurality of optimum thresholds, using a differential evolutionary optimization technique. Further the system 200 comprises a classifier 210 configured for determining the quality of the plurality of input signals at real time based on a PPG signal classification technique, wherein the quality of the plurality of input signals is determined as one of a bad signal and a good signal.

The various modules of the system 100 and the functional blocks in FIG. 2 are configured for determining quality of PPG signal are implemented as at least one of a logically self-contained part of a software program, a self-contained hardware component, and/or, a self-contained hardware component with a logically self-contained part of a software program embedded into each of the hardware component that when executed perform the above method described herein.

Functions of the components of the system 200 are explained in conjunction with functional modules of the system 100 stored in the memory 102 and further explained in conjunction with flow diagram of FIGS. 3A-3B. The FIGS. 3A-3B with reference to FIG. 1, is an exemplary flow diagram illustrating a method 300 for determining quality of PPG signal using the system 100 of FIG. 1 according to an embodiment of the present disclosure.

The steps of the method of the present disclosure will now be explained with reference to the components of the system 100 of FIG. 1 for determining quality of PPG signal and the modules 202-210 as depicted in FIG. 2 and the flow diagrams as depicted in FIGS. 3A-3B. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 302 of the method 300, a plurality of raw input signals is received at the filtering module 202 from a device. The plurality of raw input signals comprises a plurality of data sets associated with a PPG signal of a plurality of subjects.

In an embodiment, the device is a PPG quality checker deployed in an edge computing scenario to check the quality of the signal that can be directly implemented on the edge devices like smartwatch, wearables or medical devices for deducing health parameters of patients in order to infer about physiological conditions of heart, blood pressure, respiratory patterns, and so on. The device comprises a wearable, several diagnostic/health monitoring tools used in an Intensive Care Unit (ICU), and a medical grade devices.

In an example scenario, the plurality of raw input signals is collected from ICU patients using a plurality of medical grade devices at a sampling rate of 125 Hz or by using a pulse oximeter with a sampling rate of 60 Hz or by using a wrist sensor at sampling frequency of 64 Hz or another dataset at ICU from adult population at a sampling rate of 300 Hz.

In an embodiment, the received raw input signals are annotated based on an annotator tool. In an example scenario, the annotator tool is developed using a Python tool for the ease of annotating PPG segments from different datasets. The annotation application shows PPG segments of a fixed window size (5 seconds in the present example scenario) and the annotator marks the windows corresponding to clean PPG segments. The annotations for each of the above-mentioned datasets are collected from 5 annotators who have sound experience of working in the domain of PPG signal processing. Firstly, majority voting of these annotations and secondly a complete agreement-based annotation is considered as the final ground truth.

At step 304 of the method 300, the plurality of raw input signals is filtered to obtain a plurality of filtered signals at the filtering module 202. The plurality of raw input signals is filtered based on a filtering technique.

In an embodiment, the filtering technique comprises a low-pass filter including a Chebyshev filter. In an example scenario, a Chebyshev filter with a cut-off 3 Hz is utilized for filtering.

At step 306 of the method 300, a plurality of heart frequency components and a plurality of breathing frequency components are extracted at the extraction module 204. The plurality of heart frequency components and a plurality of breathing frequency components is extracted from the plurality of raw input signals and the plurality of filtered signals based on an extraction technique.

In an embodiment, $f_s$ is the sampling rate of the plurality of raw input signals, and frequency (f) and a power (P) are frequency-power outputs from Fast Fourier Transform (FFT), respectively, where FFT is commonly used to clean the noisy PPG signal analysis. The component corresponding to heart—plurality of heart frequency components is from f=0.61 to 2 Hz. Hence, the heart component, H is expressed as follows:

$$H = \frac{\sum_{f=0.61}^{2} P_f}{\sum_{f=0.2}^{3} P_f}; \tag{1}$$

wherein,

H is the plurality of heart frequency components, f is a frequency (f) associated with one of the plurality of raw input signals or the plurality of filtered signal, and P is a power (P) associated with one of the plurality of raw input signals or the plurality of filtered signal.

Similarly, the plurality of breathing frequency components is defined in the range: 0.2-0.6 Hz, and is expressed as shown below:

$$B = \frac{\sum_{f=0.2}^{0.6} P_f}{\sum_{f=0.2}^{3} P_f} \tag{2}$$

wherein,

B is the plurality of breathing frequency components, f is a frequency (f) associated with the plurality of raw input signals and the plurality of filtered signal, and P is a power (P) associated with the plurality of raw input signals and the plurality of filtered signal.

Figure 4:
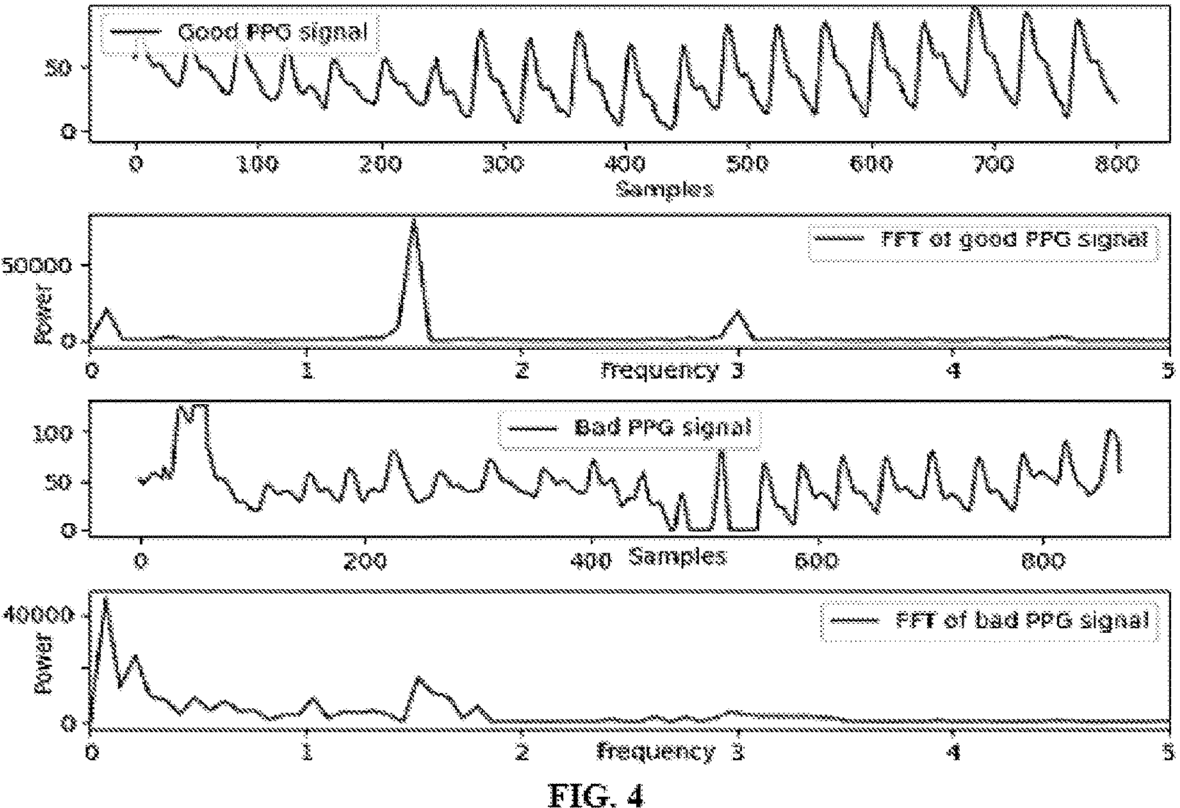
FIG. 4 is a graph illustrating a sample PPG data for clean signals and bad signals with its corresponding frequency domain view using FFT in accordance with some embodiments of the present disclosure.
Figure 5:
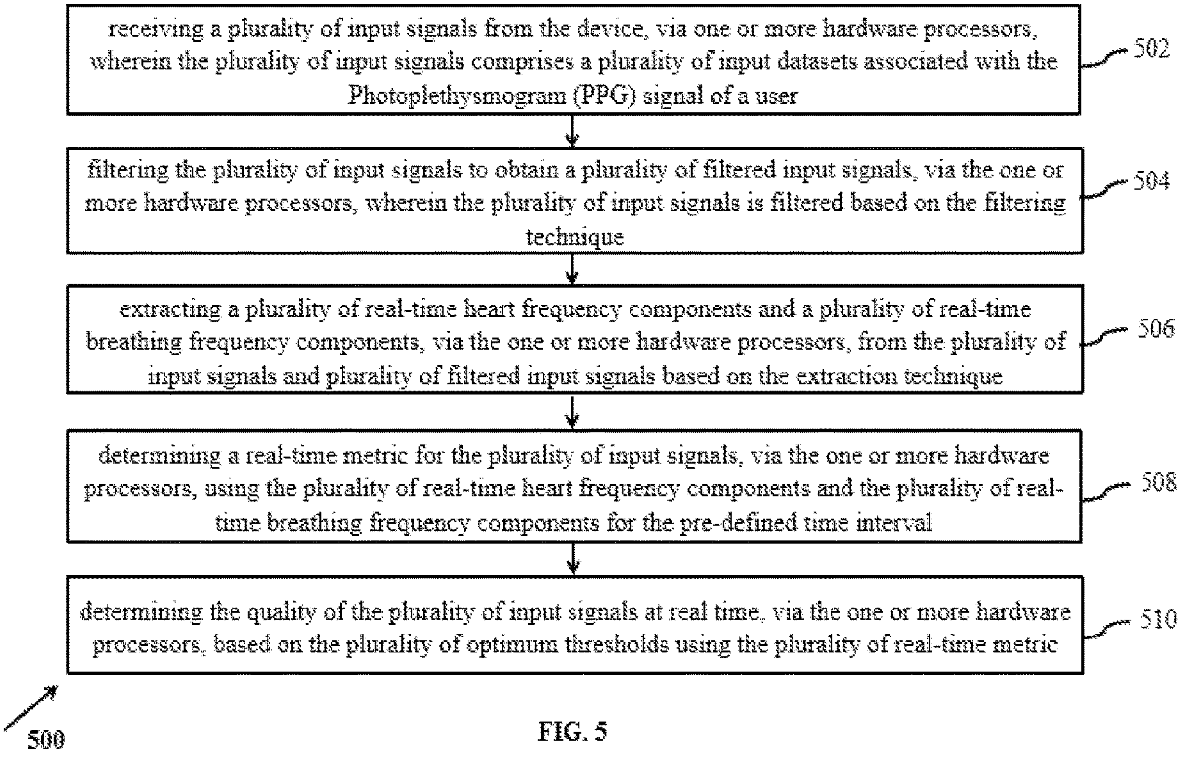
FIG. 5 is a flow diagram for PPG signal classification technique for determining the quality of the plurality of input signals in real time, using the system of FIG. 1, in accordance with some embodiments of the present disclosure.

The FIG. 4 illustrates a sample PPG data for clean signals and bad signals with its corresponding frequency domain view using FFT. It is to be noted that for a clean PPG, the dominant frequencies correspond to the heart component while lesser respiratory components are present. In case of noisy PPG, the frequencies are spread across the respiratory and heart components in an uneven manner.

At step 308 of the method 300, a plurality of metrices is determined at the metric module 206. The plurality of metrices is determined using the plurality of heart frequency components and the plurality of breathing frequency components for a pre-defined time interval.

In an embodiment, the plurality of metrices includes a mean heart component ($H_m$), a mean breathing component ($B_m$), a change in the heart component ($P_1$), and a change in the breathing component ($P_2$).

The $H_m$ and the $B_m$ is an average value of the plurality of heart frequency component and a plurality of breathing frequency component for the raw input signals and the plurality of filtered signals. The mean heart component ($H_m$) and the mean breathing component ($B_m$) is expressed as shown below:

$$H_m = \frac{H_{raw} + H_{filtered}}{2} \tag{3}$$

where, $H_{raw}$ is a heart component (H) from a raw signal $H_{filtered}$ is a heart component (H) from a filtered signal $$B_m = \frac{B_{raw} + B_{filtered}}{2} \tag{4}$$

where, $B_{raw}$ is a breathing component (B) from the raw signal $B_{filtered}$ is a breathing component (B) from the filtered signal The $P_1$ and the $P_2$ is the percentage change in the plurality of heart frequency component and a plurality of breathing frequency component for the raw input signals and the plurality of filtered signals. The change in the heart component ($P_1$) and the change in the breathing component ($P_2$) is expressed as shown below:

$$P_1 = 100 * \frac{|H_{raw} - H_{filtered}|}{H_{raw}} \tag{5}$$

$$P_2 = 100 * \frac{|P_{raw} - P_{filtered}|}{P_{raw}} \tag{6}$$

The metrics $H_m$, $B_m$, $P_1$ and $P_2$ are represented as $X_{i,j}$ (j=1; 2; 3; 4 metrics and i=1; 2; 3; :::N number of instances). For each instance $X_i$ of PPG, 4 metrics, that is—$H_m$, $B_m$, $P_1$ and $P_2$ are extracted. These metrics are used to further classify the signals into good and bad PPG segments as discussed in subsequent sections.

At step 310 of the method 300, a plurality of optimum thresholds is estimated in the optimum threshold module 208. The plurality of optimum thresholds is estimated using a differential evolutionary (DE) optimization technique.

The optimal threshold (ω) is estimated from training data for all datasets using DE optimization algorithm. The ω consists of 4 metrices ($w_j$) such that (j=1; 2; 3; 4), which corresponds to optimal thresholds for $H_m$, $B_m$, $P_1$ and $P_1$ respectively.

In an embodiment, the differential evolutionary optimization technique includes estimating a plurality of optimal thresholds ($\omega_1$, $\omega_2$, $\omega_3$, $\omega_4$) based on a pre-defined performance parameter F-Score (F) and the differential evolutionary optimization technique expressed as shown below:

$$f(\omega_1, \omega_2, \omega_3, \omega_4) = \min_{\omega_1,\omega_2,\omega_3,\omega_4} \{|1 - F|\} \tag{7}$$

$$\text{subject to } 0 \le (\omega_1, \omega_2, \omega_3, \omega_4) \le 1$$

wherein, $\omega_1$ is optimum threshold for $H_m$, $\omega_2$ is optimum threshold for $B_m$, $\omega_3$ is optimum threshold for $P_1$, $\omega_4$ is optimum threshold for $P_2$.

where, F is the F-Score of classifying the training samples into good and bad PPG classes.

At step 312 of the method 300, the quality of the plurality of input signals is determined at real time. The quality of the plurality of input signals is determined as one of bad signal and a good signal based on a PPG signal classification technique. The PPG signal classification technique is explained using the flow chart 500 as illustrated in the FIG. 5, using the system of FIG. 1. The PPG signal classification technique is explained below:

At step 502 of the method 500, a plurality of input signals is received from the device at the filtering module 202. The plurality of input signals comprises a plurality of input datasets associated with the Photoplethysmogram (PPG) signal of a user. With the arrival of the plurality of input signals, the system works in the testing phase, wherein the plurality of input signals are processed to classify the quality of the received PPG signals as one of: a good signal or a bad signal.

In an embodiment, the plurality of PPG signals associated with a Photoplethysmogram (PPG) signal include test data received from several sources including a medical diagnostic device used in hospitals, data collected from pulse oximeter and a wearable device or any wearable or a medical grade device.

At step 504 of the method 500, the plurality of input signals is filtered in the filtering module 202 to obtain a plurality of filtered input signals. The plurality of input signals is filtered based on the filtering technique.

In an embodiment, the filtering technique comprises a low-pass filter including a Chebyshev filter.

At step 506 of the method 500, a plurality of real-time heart frequency components and a plurality of real-time breathing frequency components is extracted in the extraction module 204. The plurality of real-time heart frequency components and the plurality of real-time breathing frequency components is extracted from the plurality of input signals and plurality of filtered input signals based on the extraction technique.

The component corresponding to heart—plurality of real-time heart frequency components is from f=0.61 to 2 Hz. Hence, the real-time heart component, H is expressed as follows:

$$H = \frac{\sum_{f=0.61}^{2} P_f}{\sum_{f=0.2}^{3} P_f}; \tag{8}$$

Similarly, the plurality of real-time breathing frequency components is defined in the range: 0.2-0.6 Hz, and is expressed as shown below:

$$B = \frac{\sum_{f=0.2}^{0.6} P_f}{\sum_{f=0.2}^{3} P_f} \tag{9}$$

At step 508 of the method 500, a real-time metric for the plurality of input signals is determined at the metric module 206. The real-time metric for the plurality of input signals is determined using the plurality of real-time heart frequency components and the plurality of real-time breathing frequency components for the pre-defined time interval.

In an embodiment, the plurality of metrices includes a real-time mean heart component ($H_m$), a real-time mean breathing component ($B_m$), a change in the real-time heart component ($P_1$), and a change in the real-time breathing component ($P_2$).

The $H_m$ and the $B_m$ is an average value of the plurality of real-time heart frequency component and a plurality of real-time breathing frequency component for the input signals and the plurality of filtered signals.

The $P_1$ and the $P_2$ is the percentage change in the plurality of real-time heart frequency component and a plurality of real-time breathing frequency component for the raw input signals and the plurality of filtered signals.

At step 510 of the method 500, the quality of the plurality of input signals is determined at real time based on the optimum threshold using the plurality of real-time metric at the classifier 210.

In an embodiment, for the testing phase, a function $\emptyset(.,.)$ is defined over the metrics $X_i$ (testing instances) and the optimal thresholds ($\omega$), such that, $\emptyset(X_{i,j}, \omega_j)$, ($\forall$=1,2,3,4 features in $X_i$) returns 1 when the given parameter $X_1$ is below the threshold $\omega_1$; and 0 otherwise. Thus, the predictions of classifying the test data into good and bad PPG is given by $$S_i = \prod_{\omega_j=1}^{4} \phi(X_{i,j}, \omega_j) \tag{10}$$

where, $\forall$=1,2,3,4 . . . N number of test samples. The $S_i$ is 1 for correctly classified samples, and 0 otherwise. These predictions are then used to compute the pre-defined performance parameter F-Score (F) of equation (7) using the differential evolutionary optimization technique. The annotations from 5 experts is collected and is considered to be the ground-truth.

Experimental Data:

Experiments have been conducted to understand the performance of the disclosed technique. The experiment has been conducted with multiple datasets, including few publicly available datasets such as MIMIC (Medical Information Mart for Intensive Care) and Capnobase, and some in-house collected datasets using the E4 wristband (E4) and Contec pulse oximeter (Contec).

In order to ensure consistency in the accuracy of annotations, the consistency is validated amongst the annotators/Subject matter experts (SME) by performing Krippendorff's alpha test on the annotations obtained from different annotators. Good inter-rater reliability is found as shown in Table 1.

TABLE 1

Krippendorff's alpha values for the annotation from SMEs.

| Dataset | Krippendorff's alpha |
|---|---|
| Contec | 0.8004 |
| E4 | 0.8235 |
| MIMIC | 0.7986 |
| Capnobase | 0.9093 |

The optimal values ($\omega$) is obtained for each of the datasets using DE optimization and is reported in Table 2. The $F_{score}$ of classifying the training data samples is also given. The high $F_{score}$ values are indicative of the optimality of the obtained thresholds. In an average healthy person, the heart rate is typically at least twice higher than the respiratory rate at a given point in time.

TABLE 2 optimal values ($\omega$) obtained for each of the datasets using DE optimization.

| Dataset | $H_m$ | $B_m$ | $P_1$ | $P_2$ | $F_{score}$ |
|---|---|---|---|---|---|
| Contec | 0.23 | 0.17 | 0.15 | 0.34 | 0.71 |
| E4 | 0.88 | 0.06 | 0.23 | 0.18 | 0.85 |
| MIMIC | 0.45 | 0.17 | 0.16 | 0.35 | 0.77 |

Table.3 and Table.4 show the $F_{score}$ values for classifying the good and bad PPG segments in the test data. The ground truth values were obtained based on majority voting among the annotators (Table 3) as well as full agreement among the annotators (Table 4). The legends are the $F_{score}$ for the unsupervised algorithms implemented and tested on the datasets. The legend SVM represents the implementation of Support Vector Machine and is the supervised approach tested on the datasets. Although the SVM classifier performed slightly better on the MIMIC dataset which is ICU grade data, the disclosed techniques has done better on the clinical and fitness datasets. Further is to be noted that disclosed techniques consistently out-performs the other state-of-art techniques. For the E4 wearable data, the disclosed techniques performed significantly better. Wearable device-based PPG data are more prone to noise. The strong point of the disclosed techniques is that even for data collected through wearable devices such as E4, the disclosed techniques out-performs the other algorithms significantly.

TABLE 3

Comparison of the $F_{score}$ values for classifying the good and bad PPG segments in the test data using the disclosed technique and for state-of-art techniques (GT based on majority voting).

| Dataset | SOA1 | SOA2 | SVM-based | Disclosed technique |
|---|---|---|---|---|
| Contec | 0.8004 | 0.65 | 0.47 | 0.73 |
| E4 | 0.8235 | 0.4 | 0.83 | 0.93 |
| MIMIC | 0.7986 | 0.62 | 0.83 | 0.79 |
| Capnobase | 0.9093 | 0.44 | 0.46 | 0.41 |

TABLE 4

Comparison of the $F_{score}$ values for classifying the good and bad PPG segments in the test data using the disclosed technique and for state-of-art techniques (GT based on full agreement).

| Dataset | SOA1 | SOA2 | SVM-based | Disclosed technique |
|---|---|---|---|---|
| Contec | 0.49 | 0.62 | 0.69 | 0.69 |
| E4 | 0.71 | 0.35 | 0.85 | 0.92 |
| MIMIC | 0.39 | 0.58 | 0.85 | 0.75 |
| Capnobase | 0.36 | 0.43 | 0.42 | 0.48 |

Figure 6:
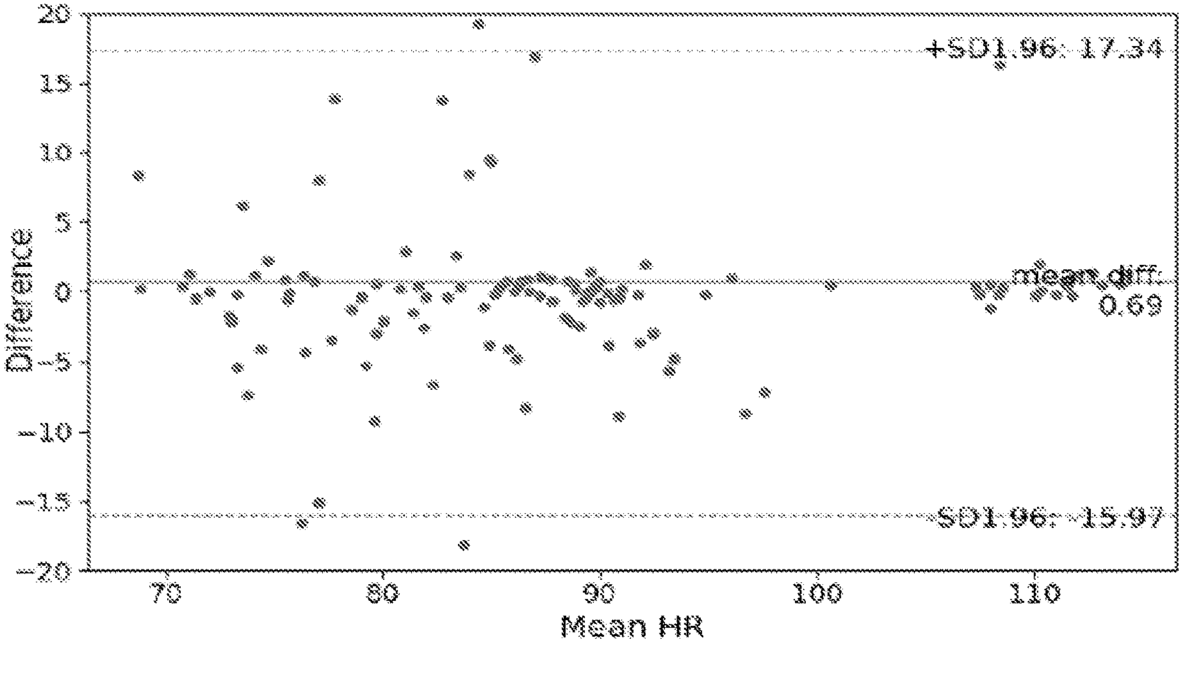
FIG. 6 is a graph illustrating a comparison plot between the HR values computed using the GT and the corresponding HR values computed derived optimal threshold (w) from using a mobile application for receiving the PPG signal in accordance with some embodiments of the present disclosure.
Figure 7:
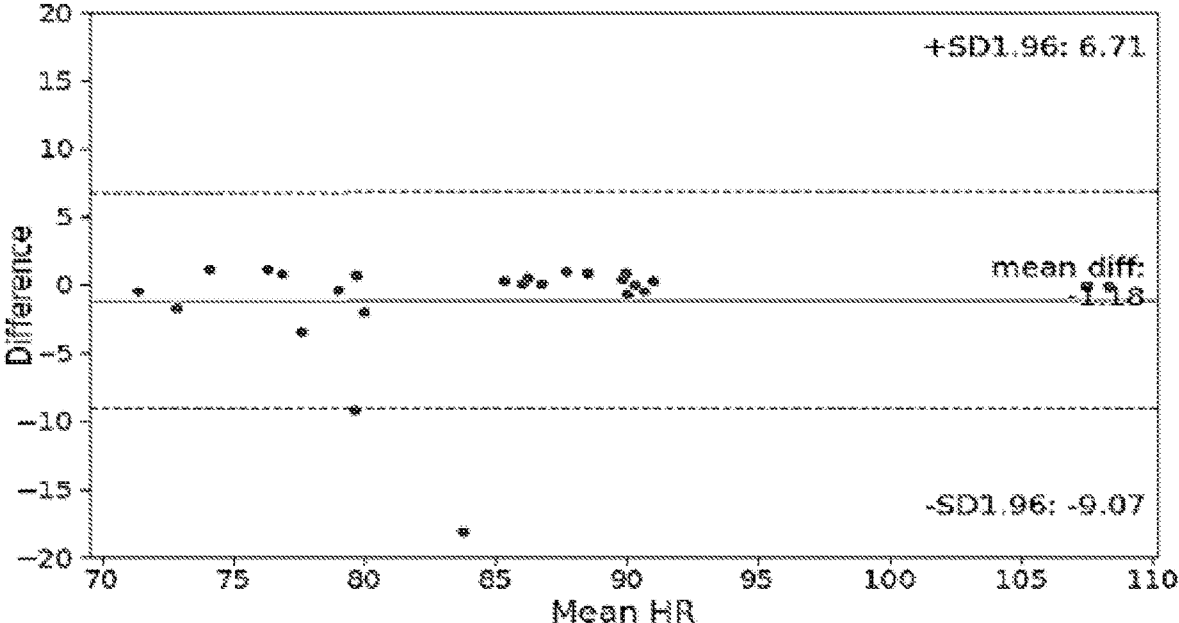
FIG. 7 is a graph illustrating the HR values computed by selecting the good quality PPG windows using a quality checker in accordance with some embodiments of the present disclosure.

Heart rate (HR) is a standard measure computed by PPG systems. In the disclosed technique HR is the measure to evaluate the effectiveness of the proposed quality checker in a noisy PPG. The Mobile PPG application is used to collect data and simultaneous ground truth (GT) PPG is collected using Contec PPG sensor. Multiple sessions of PPG is collected from different users at different time of the day, with each session being of 60 sec duration. The FIG. 6 illustrates the Bland Altman comparison plot between the HR values computed using the GT and the corresponding HR values computed from using the mobile application PPG signals. It is to be noted that the standard deviation is large and contains outliers. The FIG. 7 illustrates the HR values computed by selecting the good quality PPG windows using the quality checker. It is to be noted that the HR values are well within the range and agreeing with the HR values computed from GT PPG. Therefore, the designed quality checker can be used effectively in identifying good quality PPG signals in PPG systems in order to avoid erroneous heart rate features.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The PPG signals are extensively used for deducing health parameters of patients to infer the physiological conditions of heart, blood pressure, breathing patterns of the patients. However, analysis based on PPG signals is extremely challenging and is accurate only on high quality PPG signals. However, the existing techniques for determining quality of PPG signal (that are collected using wearable devices) require huge training or use complicated algorithms and cannot be used for real-time analysis. The disclosed methods and system for PPG quality assessment is based on the frequency domain analysis, wherein heart and respiratory components in the frequency spectrum are used effectively to derive the quality checker metric which is further used to estimate a plurality of optimal thresholds that is used for determining the quality of PPG signals at real-time.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words “comprising,” “having,” “containing,” and “including,” and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for determining quality of Photoplethysmogram (PPG) signal, comprising:

receiving a plurality of raw input signals from a device, via one or more hardware processors, wherein the plurality of raw input signals comprises a plurality of data sets associated with a PPG signal of a plurality of one or more subjects, wherein the device comprises a wearable, a plurality of medical diagnostic tools of an Intensive Care Unit (ICU), and a plurality of medical grade devices, wherein the plurality of raw input signals is collected from ICU patients using the medical grade device at a sampling rate of 125 Hz or by using a pulse oximeter with a sampling rate of 60 Hz or by using a wrist sensor at 64 Hz or dataset at the ICU from an adult population at a sampling rate of 300 Hz;

obtaining annotations of the received raw input signals of PPG segments from varied datasets in an annotator tool and the annotations correspond to marking windows of a clean PPG segment in the PPG segments considered as a ground truth;

filtering the plurality of raw input signals to obtain a plurality of filtered signals, via the one or more hardware processors, wherein the plurality of raw input signals is filtered with a low-pass Chebyshev filter at 3 Hz cut-off frequency;

extracting a plurality of heart frequency components and a plurality of breathing frequency components, via the one or more hardware processors, from the plurality of raw input signals and the plurality of filtered signals, based on an extraction technique, wherein $f_s$ is a sampling rate of the plurality of raw input signals, and frequency (f) and a power (P) are frequency-power outputs from Fast Fourier Transform (FFT), respectively, wherein the plurality of heart frequency components is in the range of 0.61-2 Hz, and the plurality of breathing frequency components is in the range of 0.2-0.6 Hz;

determining a plurality of metrices, via the one or more hardware processors, using the plurality of heart frequency components and the plurality of breathing frequency components for a pre-defined time interval, wherein the plurality of metrices includes a mean heart component ($H_m$), a mean breathing component ($B_m$), a change in the heart component ($P_1$), and a change in the breathing component ($P_2$) wherein, (a) the $H_m$ and the $B_m$ is an average value of the plurality of heart frequency component and a plurality of breathing frequency component for the raw input signals and the plurality of filtered signals, and, (b) the $P_1$ and the $P_2$ is the percentage change in the plurality of heart frequency component and a plurality of breathing frequency component for the raw input signals and the plurality of filtered signals, wherein the percentage change in the heart component ($P_1$) and the percentage change in the breathing component ($P_2$) is expressed as:

$$P_1 = 100 * \frac{|H_{raw} - H_{filtered}|}{H_{raw}};$$

$$P_2 = 100 * \frac{|P_{raw} - P_{filtered}|}{P_{raw}};$$

wherein the plurality of metrices $H_m$, $B_m$, $P_1$ and $P_2$ are represented as $X_{i,j}$ (j=1; 2; 3; 4 metrics and i=1; 2; 3; :::N number of instances), for each instance $X_i$ of PPG, 4 metrics of $H_m$, $B_m$, $P_1$ and $P_2$ are extracted;

classifying, via the one or more hardware processors, the plurality of metrics $H_m$, $B_m$, $P_1$ and $P_2$ against thresholds into a good PPG segment and a bad PPG segment;

estimating, during a training phase, a plurality of optimum thresholds, via the one or more hardware processors, using the plurality of metrices $H_m$, $B_m$, $P_1$ and $P_2$ based on a differential evolutionary optimization technique;

determining quality of a plurality of input signals at real time via one or more hardware processors, wherein the quality of the plurality of input signals is determined as one of bad signal and a good signal based on a PPG signal classification technique using the plurality of optimum thresholds, wherein the device is a PPG quality checker deployed in an edge computing scenario to check the quality of the input signal that is directly implemented on an edge device, wherein the PPG signal classification technique during the testing phase the plurality of optimum thresholds are used for determining the quality of the plurality of input signals at real time comprises:

receiving the plurality of input signals from the device, wherein the plurality of input signals comprises a plurality of input datasets associated with the Photoplethysmogram (PPG) signal of a user;

filtering the plurality of input signals to obtain a plurality of filtered input signals, the plurality of input signals is filtered based on the filtering technique;

extracting a plurality of real-time heart frequency components and a plurality of real-time breathing frequency components, from the plurality of input signals and plurality of filtered input signals based on the extraction technique;

determining a real-time metric for the plurality of input signals, using the plurality of real-time heart frequency components and the plurality of real-time breathing frequency components for the pre-defined time interval; and determining the quality of the plurality of input signals at real time during a testing phase, wherein the quality of the plurality of input PPG signals is determined as one of bad signal and a good signal based on the plurality of optimum thresholds using the plurality of real-time metric, wherein classifying the input PPG signal into good and bad PPG signal is given by:

$$S_i = \prod_{\omega_j=1}^{4} \emptyset(X_{i,j}, \omega_j),$$

where, ∀=1,2,3,4 . . . N number of test samples and the Si is 1 for correctly classified samples, and 0 otherwise and wherein the Si is used to compute the pre-defined performance parameter F-Score using the differential evolutionary optimization technique and wherein $\emptyset$ is defined over testing instance metrics $X_i$ and the optimal thresholds (ω), such that, $\emptyset$ ($X_{(i,j)}$, $\omega_j$), (∀=1,2,3,4 features in $X_i$) returns 1 when the given parameter $X_j$ is below the threshold $\omega_i$; and 0 otherwise;

collecting PPG signals by a mobile PPG application and simultaneous ground truth (GT) PPG by a PPG sensor;

computing Heart Rate (HR) values with the GT PPG and corresponding HR values with the PPG signals collected from the mobile PPG application;

selecting only good PPG signal classified by the PPG quality checker device, implemented directly on wearables or medical devices;

computing HR values by selecting only the good PPG signal and suppressing erroneous HR features; and controlling the HR values computation, displaying the computed HR values only for windows classified as the good PPG signal, and suppressing computation and output for the bad PPG signal, thereby reducing erroneous HR features during motion artifacts.

2. The method of claim 1, wherein the extraction technique for extracting the plurality of heart frequency components and the plurality of breathing frequency components, based on a frequency (f) and a power (P) associated with the plurality of raw input signals and the plurality of filtered signal and the extraction technique is expressed as shown below:

$$H = \frac{\sum_{f=0.61}^{2} P_f}{\sum_{f=0.2}^{3} P_f};$$

wherein,

H is the plurality of heart frequency components, f is a frequency (f) associated with the plurality of raw input signals and the plurality of filtered signal, and P is a power (P) associated with the plurality of raw input signals and the plurality of filtered signal, $$B = \frac{\sum_{f=0.2}^{0.6} P_f}{\sum_{f=0.2}^{3} P_f}$$

wherein,

B is the plurality of breathing frequency components, f is a frequency (f) associated with the plurality of raw input signals and the plurality of filtered signal, and P is a power (P) associated with the plurality of raw input signals and the plurality of filtered signal.

3. The method of claim 1, wherein the differential evolutionary optimization technique includes estimating a plurality of optimal thresholds ($\omega_1$, $\omega_2$, $\omega_3$, $\omega_4$) based on a pre-defined performance parameter F-Score (F), and the differential evolutionary optimization technique is expressed as:

$$f(\omega_1, \omega_2, \omega_3, \omega_4) = \min_{\omega_1,\omega_2,\omega_3,\omega_4} \{|1 - F|\}$$

$$\text{subject to } 0 \le (\omega_1, \omega_2, \omega_3, \omega_4) \le 1,$$

wherein, $\omega_1$ is optimum threshold for $H_m$, $\omega_2$ is optimum threshold for $B_m$, $\omega_3$ is optimum threshold for $P_1$, and $\omega_4$ is optimum threshold for $P_2$.

4. A system, comprising:

a memory storing instructions;

one or more communication interfaces; and one or more hardware processors coupled to the memory via the one or more communication interfaces, wherein the one or more hardware processors are configured by the instructions to:

receive a plurality of raw input signals from a device, via one or more hardware processors, wherein the plurality of raw input signals comprises a plurality of data sets associated with a PPG signal of a plurality of subjects, wherein the device comprises a wearable, a plurality of medical diagnostic tools of an Intensive Care Unit (ICU), and a plurality of medical grade devices, wherein the plurality of raw input signals is collected from ICU patients using the medical grade device at a sampling rate of 125 Hz or by using a pulse oximeter with a sampling rate of 60 Hz or by using a wrist sensor at 64 Hz or dataset at the ICU from an adult population at a sampling rate of 300 Hz;

obtain annotations of the received raw input signals of PPG segments from varied datasets in an annotator tool and the annotations correspond to marking windows of a clean PPG segment in the PPG segments considered as a ground truth;

filter the plurality of raw input signals to obtain a plurality of filtered signals, via the one or more hardware processors, wherein the plurality of raw input signals is filtered with a low-pass Chebyshev filter at 3 Hz cut-off frequency;

extract a plurality of heart frequency components and a plurality of breathing frequency components, via the one or more hardware processors, from the plurality of raw input signals and the plurality of filtered signals based on an extraction technique, wherein $f_s$ is a sampling rate of the plurality of raw input signals, and frequency (f) and a power (P) are frequency-power outputs from Fast Fourier Transform (FFT), respectively, wherein the plurality of heart frequency components is in the range of 0.61-2 Hz, and the plurality of breathing frequency components is in the range of 0.2-0.6 Hz;

determine a plurality of metrices, via the one or more hardware processors, using the plurality of heart frequency components and the plurality of breathing frequency components for a pre-defined time interval, wherein the one or more hardware processors are configured by the instructions to determine the plurality of metrices, wherein the plurality of metric includes a mean heart component ($H_m$), a mean breathing component ($B_m$), a change in the heart component ($P_1$), and a change in the breathing component ($P_2$) wherein:

(a) the $H_m$ and the $B_m$ is an average value of the plurality of heart frequency component and a plurality of breathing frequency component for the raw input signals and the plurality of filtered signals, and;

(b) the $P_1$ and the $P_2$ is the percentage change in the plurality of heart frequency component and a plurality of breathing frequency component for the raw input signals and the plurality of filtered signals, wherein the percentage change in the heart component ($P_1$) and the percentage change in the breathing component ($P_2$) is expressed as:

$$P_1 = 100 * \frac{|H_{raw} - H_{filtered}|}{H_{raw}};$$

$$P_2 = 100 * \frac{|P_{raw} - P_{filtered}|}{P_{raw}};$$

wherein the plurality of metrices $H_m$, $B_m$, $P_1$ and $P_2$ are represented as $X_{i,j}$ (j=1; 2; 3; 4 metrics and i=1; 2; 3; :::N number of instances), for each instance $X_i$ of PPG, 4 metrics of $H_m$, $B_m$, $P_1$ and $P_2$ are extracted;

classify the plurality of metrics $H_m$, $B_m$, $P_1$ and $P_2$ against thresholds into a good PPG segment and a bad PPG segment;

estimate, during a training phase, a plurality of optimum threshold, via the one or more hardware processors, using the plurality of metrices $H_m$, $B_m$, $P_1$ and $P_2$ based on a differential evolutionary optimization;

determine the quality of the plurality of input signals at real time during a testing phase, wherein the quality of the plurality of input signals is determined as one of bad signal and a good signal based on a PPG signal classification technique using the plurality of optimum thresholds, wherein the device is a PPG quality checker deployed in an edge computing scenario to check the quality of the signal that is directly implemented on an edge device, wherein the PPG signal classification technique during the testing phase the plurality of optimum thresholds are used for determining the quality of the plurality of input signals at real time comprises:

receiving the plurality of input signals from the device, wherein the plurality of input signals comprises a plurality of input datasets associated with the Photoplethysmogram (PPG) signal of a user;

filtering the plurality of input signals to obtain a plurality of filtered input signals, wherein the plurality of input signals is filtered based on the filtering technique;

extracting a plurality of real-time heart frequency components and a plurality of real-time breathing frequency components, from the plurality of input signals and plurality of filtered input signals based on the extraction technique;

determining a real-time metric for the plurality of input signals, using the plurality of real-time heart frequency components and the plurality of real-time breathing frequency components for the pre-defined time interval; and determining the quality of the plurality of input signals at real time, wherein the quality of the plurality of input PPG signals is determined as one of bad signal and a good signal based on the plurality of optimum thresholds using the plurality of real-time metric, wherein classifying the input PPG signal into good and bad PPG signal is given by:

$$S_i = \prod\nolimits_{\omega_j=1}^{4} \phi(X_{i,j}, \omega_j),$$

where, ∀=1,2,3,4 . . . N number of test samples and the $S_i$ is 1 for correctly classified samples, and 0 otherwise and wherein the $S_i$ is used to compute the pre-defined performance parameter F-Score using the differential evolutionary optimization technique and wherein $\emptyset$ is defined over testing instance metrics $X_i$ and the optimal thresholds (ω), such that, $\emptyset$ ($X_{(i,j)}$, $\omega_j$), (∀=1,2,3,4 features in $X_i$) returns 1 when the given parameter $X_j$ is below the threshold $\omega_i$; and 0 otherwise collect PPG signals by a mobile PPG application and simultaneous ground truth (GT) PPG by a PPG sensor;

compute Heart Rate (HR) values with the GT PPG and corresponding HR values with the PPG signals collected from the mobile PPG application;

select only good PPG signal classified by the PPG quality checker device, implemented directly on wearables or medical devices; and HR values by selecting only the good PPG signal and suppressing erroneous HR features compute; and control the HR values computation, displaying the computed HR values only for windows classified as the good PPG signal, and suppressing computation and output for the bad PPG signal, thereby reducing erroneous HR features during motion artifacts.

5. The system of claim 4, wherein the one or more hardware processors are configured by the instructions to perform the extraction technique, wherein the extraction technique for extracting a plurality of heart frequency components and a plurality of breathing frequency components is expressed as shown below:

$$H = \frac{\sum_{f=0.61}^{2} P_f}{\sum_{f=0.2}^{3} P_f};$$

wherein,

H is the plurality of heart frequency components, f is a frequency (f) associated with the plurality of raw input signals and the plurality of filtered signal, and P is a power (P) associated with the plurality of raw input signals and the plurality of filtered signal, $$B = \frac{\sum_{f=0.2}^{0.6} P_f}{\sum_{f=0.2}^{3} P_f}$$

wherein,

B is the plurality of breathing frequency components, f is a frequency (f) associated with the plurality of raw input signals and the plurality of filtered signal, and P is a power (P) associated with the plurality of raw input signals and the plurality of filtered signal.

6. The system of claim 4, wherein the one or more hardware processors are configured by the instructions to perform the differential evolutionary optimization technique, wherein the differential evolutionary optimization technique includes estimating a plurality of optimal thresholds ($\omega_1$, $\omega_2$, $\omega_3$, $\omega_4$) based on a pre-defined performance parameter F-Score (F) and the differential evolutionary optimization technique expressed as shown below:

$$f(\omega_1, \omega_2, \omega_3, \omega_4) = \min_{\omega_1, \omega_2, \omega_3, \omega_4} \{|1 - F|\}$$

$$\text{subject to } 0 \leq (\omega_1, \omega_2, \omega_3, \omega_4) \leq 1$$

Wherein, $\omega_1$ is optimum threshold for $H_m$, $\omega_2$ is optimum threshold for $B_m$, $\omega_3$ is optimum threshold for $P_1$, and $\omega_4$ is optimum threshold for $P_2$.

7. A computer program product comprising a non-transitory computer readable medium having a computer readable program embodied therein, wherein the computer readable program, when executed on a computing device, causes the computing device to:

receive a plurality of raw input signals from a device, via one or more hardware processors, wherein the plurality of raw input signals comprises a plurality of data sets associated with a PPG signal of a plurality of one or more subjects, wherein the device comprises a wearable, a plurality of medical diagnostic tools of an Intensive Care Unit (ICU), and a plurality of medical grade devices, wherein the plurality of raw input signals is collected from ICU patients using the medical grade device at a sampling rate of 125 Hz or by using a pulse oximeter with a sampling rate of 60 Hz or by using a wrist sensor at 64 Hz or dataset at the ICU from an adult population at a sampling rate of 300 Hz;

obtaining annotations of the received raw input signals of PPG segments from varied datasets in an annotator tool and the annotations correspond to marking windows of a clean PPG segment in the PPG segments considered as a ground truth;

filtering the plurality of raw input signals to obtain a plurality of filtered signals, via the one or more hardware processors, wherein the plurality of raw input signals is with a low-pass Chebyshev filter at 3 Hz cut-off frequency;

extracting a plurality of heart frequency components and a plurality of breathing frequency components, via the one or more hardware processors, from the plurality of raw input signals and the plurality of filtered signals, based on an extraction technique, wherein $f_s$ is a sampling rate of the plurality of raw input signals, and frequency (f) and a power (P) are frequency-power outputs from Fast Fourier Transform (FFT), respectively, wherein the plurality of heart frequency components is in the range of 0.61-2 Hz, and the plurality of breathing frequency components is in the range of 0.2-0.6 Hz;

determining a plurality of metrices, via the one or more hardware processors, using the plurality of heart frequency components and the plurality of breathing frequency components for a pre-defined time interval, wherein the plurality of metrices includes a mean heart component ($H_m$), a mean breathing component ($B_m$), a change in the heart component ($P_1$), and a change in the breathing component ($P_2$) wherein, (a) the $H_m$ and the $B_m$ is an average value of the plurality of heart frequency component and a plurality of breathing frequency component for the raw input signals and the plurality of filtered signals, and, (b) the $P_1$ and the $P_2$ is the percentage change in the plurality of heart frequency component and a plurality of breathing frequency component for the raw input signals and the plurality of filtered signals, wherein the percentage change in the heart component ($P_1$) and the percentage change in the breathing component ($P_2$) is expressed as:

$$P_1 = 100 * \frac{|H_{raw} - H_{filtered}|}{H_{raw}};$$

$$P_2 = 100 * \frac{|P_{raw} - P_{filtered}|}{P_{raw}};$$

wherein the plurality of metrices $H_m$, $B_m$, $P_1$ and $P_2$ are represented as $X_{i,j}$ (j=1; 2; 3; 4 metrics and i=1; 2; 3; :::N number of instances), for each instance $X_i$ of PPG, 4 metrics of $H_m$, $B_m$, $P_1$ and $P_2$ are extracted;

classifying, via the one or more hardware processors, the plurality of metrics $H_m$, $B_m$, $P_1$ and $P_2$ against thresholds into a good PPG segment and a bad PPG segment;

estimating, during a training phase, a plurality of optimum thresholds, via the one or more hardware processors, using the plurality of metrices $H_m$, $B_m$, $P_1$ and $P_2$ based on a differential evolutionary optimization technique;

determining quality of a plurality of input signals at real time via one or more hardware processors, wherein the quality of the plurality of input signals is determined as one of bad signal and a good signal based on a PPG signal classification technique using the plurality of optimum thresholds, wherein the device is a PPG quality checker deployed in an edge computing scenario to check the quality of the input signal that is directly implemented on an edge device wherein the PPG signal classification technique during the testing phase the plurality of optimum thresholds are used for determining the quality of the plurality of input signals at real time comprises:

receiving the plurality of input signals from the device, wherein the plurality of input signals comprises a plurality of input datasets associated with the Photoplethysmogram (PPG) signal of a user;

filtering the plurality of input signals to obtain a plurality of filtered input signals, wherein the plurality of input signals is filtered based on the filtering technique;

extracting a plurality of real-time heart frequency components and a plurality of real-time breathing frequency components, from the plurality of input signals and plurality of filtered input signals based on the extraction technique;

determining a real-time metric for the plurality of input signals, using the plurality of real-time heart frequency components and the plurality of real-time breathing frequency components for the pre-defined time interval; and determining the quality of the plurality of input signals at real time during a testing phase, wherein the quality of the plurality of input PPG signals is determined as one of bad signal and a good signal based on the plurality of optimum thresholds using the plurality of real-time metric, wherein classifying the input PPG signal into good and bad PPG signal is given by:

$$S_i = \prod_{\omega_j=1}^{4} \phi(X_{i,j}, \omega_j),$$

where, ∀=1,2,3,4 . . . N number of test samples and the $S_i$ is 1 for correctly classified samples, and 0 otherwise and wherein the $S_i$ is used to compute the pre-defined performance parameter F-Score using the differential evolutionary optimization technique and wherein ∅ is defined over testing instance metrics $X_i$ and the optimal thresholds (ω), such that, ∅ ($X_{(i,j)}$, $\omega_j$), (∀=1,2,3,4 features in $X_i$) returns 1 when the given parameter $X_j$ is below the threshold $\omega_i$; and 0 otherwise, collecting PPG signals by a mobile PPG application and simultaneous ground truth (GT) PPG by a PPG sensor;

computing Heart Rate (HR) values with the GT PPG and corresponding HR values with the PPG signals collected from the mobile PPG application; and selecting only good PPG signal classified by the PPG quality checker device, implemented directly on wearables or medical devices computing HR values by selecting only the good PPG signal and suppressing erroneous HR features; and controlling the HR values computation, displaying the computed HR values only for windows classified as the good PPG signal, and suppressing computation and output for the bad PPG signal, thereby reducing erroneous HR features during motion artifacts.

* * * * *